United States Patent [19]

Satterlee et al.

[11] 4,009,390
[45] Feb. 22, 1977

[54] PROCESS FOR MEASURING TENDERNESS OF COOKED MEAT
[75] Inventors: Lowell Duggan Satterlee; Roy Gary Arnold, both of Lincoln; Philip C. Anderson, Crete, all of Nebr.
[73] Assignee: The Regents of the University of Nebraska, Lincoln, Nebr.
[22] Filed: Oct. 23, 1975
[21] Appl. No.: 625,251
[52] U.S. Cl. .......................... 250/273; 73/432 R; 23/230 B; 250/252
[51] Int. Cl.$^2$ .................................. G01M 23/223
[58] Field of Search .......... 250/272, 273, 358, 252; 73/432 R; 23/230 B

[56] References Cited
UNITED STATES PATENTS
2,992,332   7/1961   Madigan ........................ 250/358

Primary Examiner—Saxfield Chatmon, Jr.
Assistant Examiner—B. C. Anderson
Attorney, Agent, or Firm—Vincent L. Carney

[57] ABSTRACT

To predict the tenderness of cooked meat, the concentrations of certain trace elements such as copper, cobalt, iron, zinc, calcium, selenium and silicon and sometimes cadmium and lead in uncooked meat muscle are measured in samples taken from the carcass of the animals and samples from the same muscle are cooked and rated by a sensory taste panel (STR scores). A formula is obtained by multiple linear regression of the data using the concentrations of trace elements as the independent variables and STR as the dependent variable. To grade a carcass the concentrations of measured trace elements are entered into the formula and a predicted STR is calculated. The ratio of the concentration of iron to zinc provides an especially suitable independent variable because of its high correlation with tenderness and the ease of measuring zinc and iron accurately.

22 Claims, 2 Drawing Figures

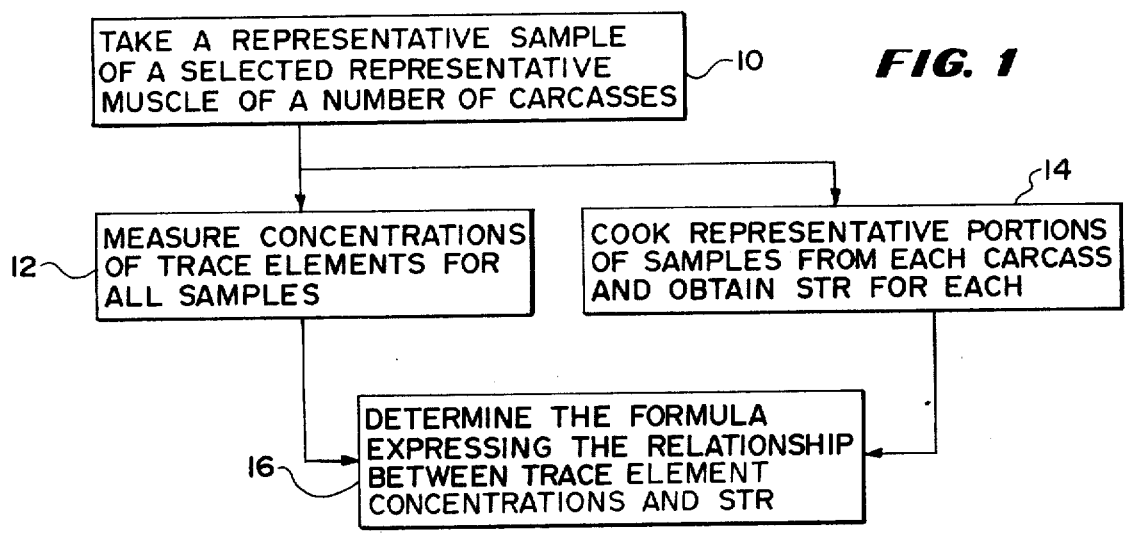
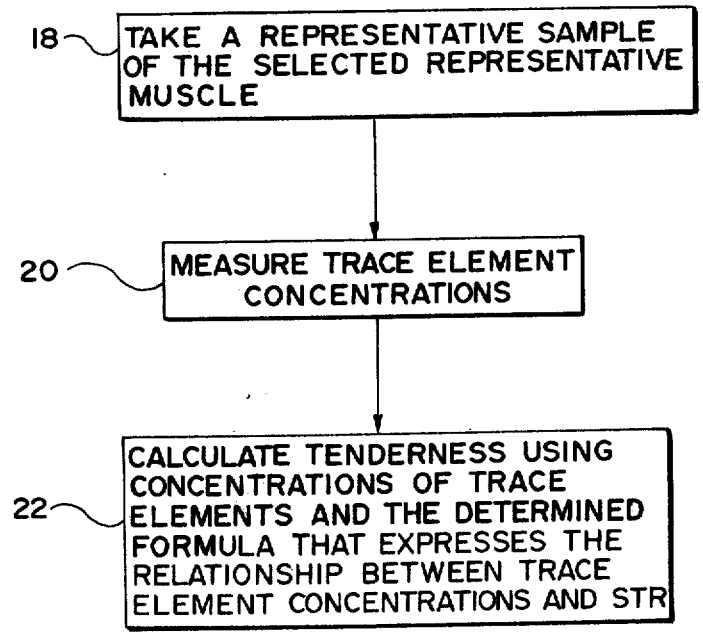

PROCESS FOR MEASURING TENDERNESS OF COOKED MEAT

This invention relates to methods of predicting the tenderness of cooked muscles of an animal from data obtained by chemical analysis of representative samples of a representative muscle from the same animal.

Beef is graded in an effort to provide standards by which the consumer may judge the quality of cooked beef from grading based on the uncooked meat. One primary characteristic of beef which is graded is the tenderness or toughness of the meat. The tenderness of the meat is related to the texture of the meat.

The purpose of grading beef is to predict the quality of the meat that the consumer is about to purchase in a way easily understood by the consumer. This information is also useful to producers and researchers. There are several different grading systems in use for beef but no system has yet been shown to be sufficiently superior to the others so that it could eventually become an international standard.

A sensory method utilizing taste-testing of meat is practiced. This provides a standard against which other grading methods may be evaluated and compared. This standard is known as a "standard taste-panel response" which rates meat in accordance with scales known as standard taste-panel responses (STR). Correlation between the results of a given testing method and the responses of standard taste-panels is an indication of the usefulness of the given testing method.

In the prior art, there are both visual and mechanical grading systems for meat and some work has been done with proposed chemical methods of grading beef.

A visual process for grading beef is widely used in the United States. In this process, the quality of the beef is graded according to the relative abundance of fat dispersion in the muscle of the beef. This estimate results in a marbling abundance score which is used to convey the quality of the beef to the consumer.

The visual grading of beef has the disadvantages of being sometimes expensive, unreliable and of providing results having a poor correlation to STR. It may be expensive because trained observers must perform the grading and it is a relatively slow system of grading. It is unreliable because it is subjective and therefore changeable. One reason that the visual grading of beef provides results having a poor correlation to STR is that it is based on a visual estimate of the amount of fat dispersion in the muscle and the visual observation of the amount of fat dispersion in the beef muscle is not directly related to the characteristics that a consumer desires in beef, the predominant characteristic being tenderness.

There are a number of different mechanical systems for testing the tenderness of meat. They are generally referred to as tenderometers. Tenderometers generally measure the force required for a cutting edge to penetrate the meat or cut the meat or the breaking resistance of the meat or other such mechanical characteristics. Some tenderometers give fairly reproducible results but still do not provide a sufficiently high correlation with the results of a sensory taste panel.

Studies of meat tenderness from a chemical point of view have generally been directed to the amount and nature of connective tissue and to the protein-ion relationships in the muscle. The prior art methods of chemical study of tenderness have had the disadvantage of not providing useful information.

Accordingly, it is an object of the invention to provide a novel method for predicting the tenderness of meat.

It is a still further object of the invention to provide a novel method for predicting the tenderness of beef.

It is a still further object of the invention to provide a novel method for grading meat which is objective, economical and provides results corresponding with STR.

It is a still further object of the invention to provide a novel chemical method for grading meat.

In accordance with the above and other objects of the invention, samples of muscle are taken from the carcass of an animal and the concentrations of certain trace elements in the samples are measured by appropriate means such as spectrophotometry or X-ray fluorescence examination. Typical trace elements which may be measured are copper, cobalt, iron, zinc, calcium, selenium and silicon, and sometimes cadmium and lead. The tenderness of cooked meat from the same animal is predicted by calculating a value corresponding to a STR from an empirical relationship between tenderness and trace elements concentrations.

To obtain the empirical relationship for a type of meat such as beef, the concentration of these elements is obtained in each of a number of representative samples taken from different carcasses but from the same representative muscle in each carcass. This concentration may be obtained by measurement of the wet sample or by drying the sample before measuring the trace elements. Corresponding samples of the muscles are cooked and rated by a standard taste panel. A formula is obtained which expresses the relationship between the concentrations of the trace elements and the STR from the taste panel, by using multiple linear regression analysis of ratios of the elements and STR or of concentrations of trace elements and STR. Formulas obtained by this process for beef have been used to predict STR with a 99% correlation.

A particularly useful formula is obtained expressing the relationship between the ratio of iron to zinc in beef and the tenderness of the beef. This relationship is particularly useful because: (1) iron and zinc can be more accurately measured than many other elements; (2) this relationship has a sufficiently high correlation with STR; and (3) the grading of beef is of exceptional commercial significance.

After the relationship between trace elements and tenderness has been determined, carcasses are graded by extracting a sample of the selected representative muscle, measuring the trace element concentrations in the sample and calculating the predicted tenderness of the meat in the carcass from the relationship between the trace elements and STR.

This method of grading meat tenderness of beef has the advantages of being: (1) objective; (2) providing a high correlation with STR; and (3) being suitable as an international standard because of its high correlation and objectivity.

The above noted and other features of the invention will be better understood from the following detailed description when considered with reference to the drawings in which:

FIG. 1 is a flow diagram of a process for determining a formula which expresses the relationship between trace element concentrations and the tenderness of meat in accordance with an embodiment of the invention; and FIG. 2 is a flow diagram of a process for grading meat in accordance with the invention using the formula which expresses the relationship determined by the process of FIG. 1.

Broadly, the preferred embodiment of the invention includes a first process illustrated in FIG. 1 to determine the mathematical relationship between trace element concentrations in a type of animal from samples taken from several carcasses of that type of animal and thereafter using a second process illustrated in FIG. 2 to grade carcasses of that type of animal by taking a similar sample from the carcass being graded, measuring the trace element concentrations in the sample and grading the carcass using the formula expressing the relationship obtained in the first process.

As shown in FIG. 1, the relationship between the trace element concentrations and standard taste responses is determined from a process that includes: (1) the step 10 of obtaining representative samples of a representative muscle from a number of different carcasses of the same species of animal; (2) the step 12 of measuring the concentrations of certain trace elements in each of the samples; (3) the step 14 of obtaining STR for the same carcasses for which the concentrations of the trace elements were obtained; and (4) the step 16 of determining the formula that expresses the relationship between trace element concentrations and STR for the type of meat of the carcass.

In obtaining samples to calculate the relationship between trace elements and STR, a representative sample of the same muscle is sampled from several carcasses. For example, the whole hearts of cattle may be used to calculate the relationship between the STR of cooked beef and the concentrations of those trace elements in the heart muscle of cattle. In selecting a muscle to be used for establishing the relationship between trace elements in the meat and the tenderness of the meat a muscle is selected which is inexpensive and conveniently obtained so that the relationship may be inexpensively used to grade uncooked meat for consumers. Although the concentrations of the trace elements are not the same in every muscle of a carcass, any suitable muscle may be used, provided the same muscle is used for each carcass to be graded or used to determine the relationship for grading.

Of course, different formulas expressing the relationships must be determined for each different species of animal to be graded and for each different muscle to be used as the grading standard for samples. For example, a formula expressing the relationship between STR and trace elements for beef does not apply to poultry or pork. Within a given species, one formula is sufficient to express the relationship between trace element concentrations and STR for all breeds. Particular formulas expressing the relationship between concentrations of trace elements and STR can, however, be determined for other types of animals by the same process used to calculate this relationship for beef. Moreover, it is possible in some instances to grade using a sample from a different muscle than that used to establish the relationship, provided the muscle used in grading has concentrations of trace elements that can be accurately correlated with the concentrations of the trace elements in the muscle that was taken as the sample to establish the formula expressing the relationship between the trace elements and the STR. A particularly suitable muscle for cattle is the muscle Longissimus Dorsi at the twelfth rib because it is easy to obtain.

Generally, the formula is obtained from wet samples of uncooked meat taken from a number of carcasses such as ten. The concentration is usually expressed in terms of parts per million of dry matter even though measured from a wet sample and then corrected for moisture. However, the meat may be ashed or dried or altered in any manner that still permits the measurement of the concentrations of the trace elements, and a larger or smaller number than 10 carcasses can be used. The larger the number of carcasses used to establish the relationship, the greater is the precision of the correlation.

The step 12 of measuring the concentrations of trace elements in the samples of carcasses is performed using any of several known techniques and combinations of techniques. The trace elements which are so measured include copper, cobalt, iron, zinc, calcium, selenium and silicon, and sometimes cadmium and lead. Cadmium and lead are pollutants which affect calcification but are not always present or ordinarily present in very low concentrations, and therefore ordinarily of relatively minor relevance.

The choice of the measuring technique depends on the elements that are to be measured and the equipment that is available for the measurements. For example, the samples may be dissolved in hydrochloric acid and certain trace elements such as calcium, zinc, iron, lead, cadmium, cobalt and copper can be measured with absorption spectroscopy. Other special techniques are used to measure selenium and silicon because of their low sensitivity to atomic absorption techniques.

Certain trace elements are measured because it has been found that there is a relationship between the tenderness of meat and the concentrations of these trace elements in the meat. A closer correlation is obtained when more than two of the elements are used and a relationship is determined either with the trace elements as separate terms of an equation, ratios to each other, groups of ratios, factors or groups of factors.

Trace elements are elements that are found in small percentages within the muscle. Some of them provide closer correlations than others. One ratio of trace elements which provides an unexpectedly good correlation and which is especially suitable for measurements because of the large quantities found in the muscle is the ratio of iron to zinc. Both iron and zinc are found in quantities such as a hundred parts per million of dry matter whereas other trace elements for which a correlation has been found are on the order of ten parts per million. Consequently, the ratio of iron to zinc is especially suitable for use in establishing standards for the grading of meat.

An especially suitable measurement for iron and zinc can be made by homogenizing the uncooked tissue by any mechanical means including the use of a sonic device. In this measuring technique, the homogenate is pressed against a Mylar film and the air bubbles are encouraged to escape from the Mylar film's surface by vibration thus insuring a good surface for the testing procedure. The sample, thus prepared, is excited by Bremsstrahlung or other radiation from an X-ray tube and the fluorescence photons of the iron and zinc atoms are captured and recognized, quantified and reported using EDAX equipment or the equivalent thereof. EDAX equipment is manufactured by EDAX International Incorporated, Prairie View, Illinois. This measures the concentrations of iron and zinc which may be used directly to determine the formula expressing the relationship between the STR and the concentrations of these elements. After the formula has been determined these measures may be used to grade carcasses by calculating an STR representing tenderness from the determined relationship of the individual concentrations of iron and zinc or their ratios with the STR.

The step 14 of cooking a portion of samples from each animal and obtaining STR for the sample is performed using known and standardized methods and conditions. The STR are ratings provided by standardized taste panels. A scale is used and this scale may be arbitrarily selected.

Standard taste panels are groups of trained personnel who taste samples of cooked meat under standard conditions and rate the cooked meat. The procedure provides a known standard against which tenderness measuring techniques can be compared. The panel rates the particular quality of meat being tested on a given hedonistic scale. For example, a goodness scale of one to five may be used with one being selected for the lowest rating and five for the highest rating. The STR provides the closest possible measurement standards to those of an ordinary consumer.

The step 16 of determining the formula which expresses the relationship between the trace element concentrations and STR employs known mathematical techniques. An especially suitable technique is stepwise multiple linear regression analysis which may be performed in accordance with standard computer programs or may be done by hand. In performing such an analysis, the concentrations of trace elements, ratios of trace elements or multiple factors of trace elements are used as the independent variables and the STR as the dependent variables. Any range of hedonistic values may be selected and corresponding different equations with different coefficients are obtained. A hedonistic standard having a range of from one to five has been conveniently related to the ratio of the concentrations of iron to zinc to obtain particularly useful formulae.

Of course, the same muscles or groups of muscles should be used in all of the samples to obtain a meaningful correlation but muscles having similar concentrations of trace elements may be substituted for each other and muscles for which the concentrations of trace elements are related in a known way may be substituted for each other and the differences in concentration accounted for mathematically so that the correlation may be obtained from a mixed group of muscles or from a similar muscle such as the heart whereas samples are actually taken in the carcasses that are being rated after the relationship between the trace elements and STR has been determined.

It is not known why suitable equations are obtained using standard multiple linear regression analysis procedures in which a set of STR values are the dependent variables and each set of trace element concentration values are independent variables or in which the set of STR values is the dependent variable and the varous possible ratios or factors of the elemental concentrations are the independent variables. However, it is believed that this relationship occurs because the trace elements indicate the extent of calcification of the muscle tissue which has occurred during the life of the animal as its age increases and as its diet has included these elements. The elements studied are known to affect calcification of biological tissues.

This relationship between tissue calcification and toughness is assumed because the toughness of meat is increased with age and with certain diets as a result of chemical changes taking place in the connective tissue of the muscle. The chemical change is indicated in the increased calcification of the connective tissue with time. A possible reason for the relationship between calcification and the toughness of meat is discussed on page 291 of Bloom, William and Fawcett, Don W.: A Textbook of Histology 9th Edition, W. B. Saunders Company, Philadelphia 1968. Therefore it is believed that the amount of the trace elements affects the toughness of the meat.

These elements include iron, calcium, cobalt, copper, selenium, silicon and zinc, and sometimes cadmium and lead. It was known that these elements are found in meat. It is believed that the ratio of iron to zinc is particularly well correlated to tenderness because zinc increases the amount of marbling which inhibits calcification, and the iron decreases marbling by promoting its oxidation thereby allowing calcification to increase.

Zinc is a constituent of insulin and aids in the conversion of blood glucose to glycogen and therefore to the syntheses of adipose tissue from blood glucose. Consequently the amount of marbling increases with the amount of zinc. The ratio of iron to fat free muscle is nearly constant. Accordingly the iron to zinc ratio is an inverted fraction closely related to the marbling to meat ratio.

A similar measuring technique is applicable to meats in general since toughness in meats is related to calcification of connective tissue in all meats. Consequently, this technique should yield suitable relationships for swine or poultry.

It is a surprising result that such high correlations are obtainable between trace element concentrations and tenderness. It is synergistic that the ratio of the two elements, iron and zinc, which are easiest to measure with accuracy should be suitable and provide a sufficiently high correlation.

The calculations may be made according to any standard step-wise multiple linear regression analysis technique such as that described in Ezekiel M. METHODS OF CORRELATION ANALYSIS, Second Edition, John Wylie and Sons, 1941 and computer programs are available for performing these calculations.

Particular formulas have been obtained using several of the elements for beef and these formulas have been derived from the tenderness results of a standard test panel. A high correlation has been obtained between the trace element concentrations and tenderness (STR) and a lesser correlation between measurements with a tenderometer and tenderness (STR). This indicates that the chemical tests in accordance with this invention provide better predictability to the standard test panel than the mechanical texture test used for this comparison.

After a relationship has been determined between two or more of the trace element concentrations of ratios thereof and the STR, it is possible to grade meat from carcasses using samples taken from the meat in accordance with the process illustrated by the flow diagram in FIG. 2.

In this process, an uncooked sample is taken of a muscle of each carcass to be graded which muscle is preferably the same muscle used in determining the formula which expresses the relationship between the trace element concentrations and the STR as shown at step 18 in FIG. 2. After obtaining suitable samples, the step of measuring trace element concentrations in the sample shown by the block 20 in FIG. 2 is performed. The same trace element concentrations which are the independent variables in the formula to be used are determined and entered into the formula. This concentration or ratio of concentrations or product of concentrations is entered into the formula and a calculation made of the STR in accordance with step 22 in the flow diagram of FIG. 2.

EXAMPLES

The following non-limitative examples illustrate the invention.

GENERAL CONDITIONS

The samples used for the examples were taken from the same muscle in ten carcasses. More specifically the samples were five gram shavings from the muscle semi-membranosus of cattle.

For each of the examples, a sensory test panel which included nine panelists simultaneously judged the tenderness and juicyness of cooked beef muscle. The judgements were made on a five-point continuous hedonic scale from excellent with a rating of five down to poor with a rating of one. The mean tenderness score for each sample was the mean of all values reported by the panel for that sample expressed as a decimal value of units, tenths and hundredths. The specific conditions of this entire procedure have been reported in the thesis for degree of Master of Science of Mr. Leslie Vavak, the University of Nebraska, Department of Food Technology, Lincoln, Nebraska, 1975. This book is in the University of Nebraska Library.

An evaluation of samples taken from the same muscles was obtained from a rotating knife tenderometer. The instrument used was that manufactured by Feed Service Company and described in Anderson, P. C., Rapp, J. L. C. and Costello, D. F., 1972, ROTATING DULL KNIFE TENDEROMETER, Food Technol. 26 (1:25–30). Seven of the nine elements of interest were analyzed by atomic absorption spectrophotometry. These are: calcium, cadmium, cobalt, copper, iron, lead and zinc. A dry ashing technique was applied for the distribution of organic matter. The moisture content of the samples were each determined prior to the measurement of the residual elements.

Data was obtained indicating a correlation between the trace elements and the tenderness of the meat as determined by standard test panel responses by a tenderometer. This data is shown in Table I.

In preparing the samples for measuring any of the trace elements calcium, zinc, iron, lead, cadmium, cobalt and copper, the samples were dissolved in 50% HCl while heating to a medium heat.

For the calcium and zinc determinations with absorption spectrophotmetry, two grams of the dry sample were diluted to 100 milliliters volume. Then they were further diluted with 40 milliliters sample solution being added to a 10 milliliter lanthanum (5% solution) into a 100 milliliter volume. The final dilutions were two grams dissolved in 100 milliliters which was then diluted with 40 milliliters of the solution being put in 100 milliliters of 5 percent lanthanum which is equal to 125 milliliters per liter gram (dry) of one percent lanthanum solution. In other words, the dilution factor is approximately 125.

TABLE I

|  | 1 | 2 | 3 | 4 |
|---|---|---|---|---|
| STR | 4.23 | 3.71 | 4.26 | 4.02 |
| Rotating Knife Tenderometer | .52 | .64 | .80 | .48 |
| Cobalt % | .000042 | .000044 | .000041 | .000044 |
| Copper % | .000079 | .000081 | .000079 | .000070 |
| Iron % | .0025 | .0021 | .0026 | .0023 |
| Zinc % | .0038 | .0056 | .0053 | .0040 |
| Calcium % | .0054 | .0065 | .0054 | .0054 |
| Silicon % | .0047 | .0043 | .0040 | .0054 |

|  | 5 | 6 | 7 | 8 |
|---|---|---|---|---|
| STR | 3.23 | 3.07 | 3.62 | 1.71 |
| Rotating Knife Tenderometer | .57 | .29 | .62 | .22 |
| Cobalt % | .000045 | .000041 | .000044 | .000046 |
| Copper % | .000099 | .000077 | .000097 | .000084 |
| Iron % | .0031 | .0025 | .0027 | .0032 |
| Zinc % | .0049 | .0033 | .0045 | .0039 |
| Calcium % | .0053 | .0048 | .0051 | .0055 |
| Silicon % | .0045 | .0050 | .0050 | .0047 |

|  | 9 | 10 |
|---|---|---|
| STR | 2.23 | 1.34 |
| Rotating Knife Tenderometer | .22 | .28 |
| Cobalt % | .000043 | .000045 |
| Copper % | .000073 | .000088 |
| Iron % | .0035 | .0031 |
| Zinc % | .0037 | .0031 |
| Calcium % | .0049 | .0053 |
| Silicon % | .0043 | .0047 |

For the iron measurement, two grams of dry samples were diluted to 100 milliliters volume. This provides a dilution factor of approximately 50. For the lead, cadmium, cobalt and copper, 10 grams of dry sample were diluted to 50 milliliters of volume or 5 grams dry sample were diluted to 25 milliliters of volume.

Selenium was measured by other methods. The method selected was the method described by Cummings, L. M., Martin, J. L. and Maag, D. D., 1965, AN IMPROVED METHOD FOR DETERMINATION OF SELENIUM IN BIOLOGICAL MATERIAL, Analyt. Chem 37:430.

To determine the amount of silicon, approximately three to four grams of wet muscle tissue were dried and ashed and reduced to solution. One method for accomplishing this is described in Rainwater, F. H. and Thatcher, L. L., 1960, METHODS FOR COLLECTION AND ANALYSIS OF WATER SAMPLES: Geological Survey Water Supply Paper, 1454, Washington, U.S. Government Printing Office, 259.

An iron to zinc ratio is obtainable by a superior method. This method is to homogenize the sample and press it against a Mylar film. The air bubbles are removed from the surface by vibrating the surface. The sample, thus prepared, is excited by Bremsstrahlung or other radiation from an X-ray tube and the fluorescence of the iron and zinc atoms measured by EDAX equipment or the like.

This technique is fast, subject to automation and provides accurate results. X-ray fluorescence examination requires less than one minute per sample. When the ratio of iron to zinc is used as the independent variable, this ratio should be measured with an error of less than plus or minus two percent although five percent is tolerable.

Iron, selenium and cobalt concentrations yield statistically significant correlations ($r$=20.5–0.8) with sensory panel tenderness responses and lead yields a statistically significant correlation ($r = -0.66$). Zinc does not yield significant correlations by itself. All correlations are relatively low to be used as an accurate standard for grading meat.

However, when a step-wise multiple regression analysis is performed, correlation coefficients are obtained which are sufficiently close to be used to predict the responses of a sensory taste panel and to be used for grading meat. These results show a close correlation when the percentage of the element is based on dry weight of the tissue rather than on the wet weight, with both the response of the sensory taste panel and a tenderometer. A suitable regression to be used is described in Cochran, Cox EXPERIMENTAL DESIGNS, John Wylie and Sons, Inc., New York, 1968, Second.

EXAMPLE 1

The concentrations of calcium, iron, silicon and zinc were measured as described above and STR were obtained from samples of the same muscles. Coefficients were obtained from a computer run of multiple step regression with STR values being one to five and the independent variables being the ratios of iron to calcium, iron to zinc and silicon to calcium. Formula A was obtained. All percentages were measured from dry samples and corrected to wet samples. The STR calculated in this example corresponds to the measured STR as shown in Table II.

EXAMPLE 2

The concentrations of iron, silicon, zinc and calcium were measured and the STR are obtained as described above. The coefficients were obtained from a multiple step-wise regression on a computer program with the concentrations of iron, silicon, zinc and calcium as the independent variables and the STR responses as the dependent variable. Formula B was obtained. The calculated STR correspond to the measured STR as shown in Table III.

TABLE II

FORMULA A $$STR = 4.1076 \times 1 - 5.6932 \frac{iron}{zinc} + 1.1783 \frac{iron}{calcium} + 2.6509 \frac{silicon}{calcium}$$

| Animal Number | Actual STR | Calculated STR |
|---|---|---|
| 1 | 4.23 | 3.22 |
| 2 | 3.71 | 4.11 |
| 3 | 4.26 | 3.85 |
| 4 | 4.02 | 3.99 |
| 5 | 3.23 | 3.45 |
| 6 | 3.07 | 3.17 |
| 7 | 3.62 | 3.91 |
| 8 | 1.71 | 2.39 |
| 9 | 2.23 | 1.89 |
| 10 | 1.34 | 1.45 |

TABLE III

FORMULA B $$STR = +.0772 \text{ zinc} - .1362 \text{ calcium} - .1933 \times iron\% - .0116 \times silicon\% + 13.0741 \times 1$$

| Animal Number | Actual STR | Calculated STR |
|---|---|---|
| 1 | 4.23 | 0.3269E 01 |
| 2 | 3.71 | 0.3981E 01 |
| 3 | 4.26 | 0.4315E 01 |
| 4 | 4.02 | 0.3728E 01 |
| 5 | 3.23 | 0.3117E 01 |
| 6 | 3.07 | 0.3665E 01 |
| 7 | 3.62 | 0.3796E 01 |
| 8 | 1.71 | 0.1856E 01 |
| 9 | 2.23 | 0.1984E 01 |
| 10 | 1.34 | 0.1704E 01 |

EXAMPLE 3

The concentrations of iron, cobalt, silicon and zinc were measured as described above and the STR were obtained. The same multiple step-wise computer program was used with the ratios of iron to cobalt, silicon to cobalt and iron to zinc as the independent variables and the STR as the dependent variables. The coefficients are shown in Formula C and the measured and calculated STR are shown in Table IV.

EXAMPLE 4

The concentrations of iron and zinc were measured as described above and the STR were obtained. The same multiple step-wise computer program was used with the ratios of iron to zinc as the independent variables and the STR as the dependent variables. The coefficients are shown in Formula D and the measured and calculated STR are shown in Table V.

EXAMPLE 5

The concentrations of calcium, cadmium, lead, cobalt, copper, zinc, iron and selenium were measured and described above and the STR were obtained. The same multiple step-wise computer program was used with the concentrations of calcium, cadmium, lead, cobalt, copper, zinc, iron and selenium as the independent variables and the STR as the dependent variables. The coefficients are shown in Formula E and the measured and calculated STR are shown in Table VI.

TABLE IV

FORMULA C $$STR = .0543 \times \frac{iron\%}{cobalt\%} + .0503 \times \frac{silicon\%}{cobalt\%} - 6.6418 \times \frac{iron\%}{zinc\%} - 1.1557 \times 1$$

| Animal Number | Actual STR | Calculated STR |
|---|---|---|
| 1 | 4.23 | 3.35 |
| 2 | 3.71 | 3.87 |
| 3 | 4.26 | 3.95 |
| 4 | 4.02 | 4.05 |
| 5 | 3.23 | 3.42 |
| 6 | 3.07 | 3.27 |
| 7 | 3.62 | 3.92 |
| 8 | 1.71 | 2.32 |
| 9 | 2.23 | 2.03 |
| 10 | 1.34 | 1.20 |

TABLE V

FORMULA D $$STR = -4.5199 \times \frac{iron\%}{zinc\%} + 6.2386 \times 1$$

| Animal Number | Actual STR | Calculated STR |
|---|---|---|
| 1 | 4.23 | 3.26 |
| 2 | 3.71 | 4.54 |
| 3 | 4.26 | 4.02 |
| 4 | 4.02 | 3.63 |
| 5 | 3.23 | 3.38 |
| 6 | 3.07 | 2.81 |
| 7 | 3.62 | 3.52 |
| 8 | 1.71 | 2.53 |
| 9 | 2.23 | 1.96 |
| 10 | 1.34 | 1.71 |

TABLE VI

FORMULA E $$STR = -0.1054 \times \%calcium \times 10^4 - 59.0651 \times \%cadmium \times 10^4$$
$$- 0.7538 \times \%lead \times 10^4 + 4.9301 \times \%cobalt \times 10^4$$
$$- 3.2299 \times \%copper \times 10^4 + 0.1065 \times \%zinc \times 10^4$$
$$- 0.0806 \times \%iron \times 10^4 + 4.0808 \times \%selenium \times 10^4$$
$$+ 9.7360 \times 1$$

| Animal Number | Actual STR | Calculated STR |
|---|---|---|
| 1 | 4.23 | 4.21 |
| 2 | 3.71 | 3.75 |
| 3 | 4.26 | 4.17 |
| 4 | 4.02 | 3.98 |
| 5 | 3.23 | 3.33 |
| 6 | 3.07 | 3.19 |
| 7 | 3.62 | 3.53 |
| 8 | 1.71 | 1.75 |
| 9 | 2.23 | 2.22 |
| 10 | 1.34 | 1.24 |

As can be understood from the above description, the method of this invention has the advantages of being: (1) objective since it is based on measurements rather than visual observation; (2) providing a high correlation with STR; and (3) being suitable as an international standard because of its high correlation and objectiveness. Moreover, when the ratio of iron to zinc is used as the independent variable, grading may be done quickly and inexpensively.

Although specific examples have been described with particularity, many modifications of the examples are possible in the light of the above teachings. It is therefore to be understood that, within the scope of the apended claims the invention may be practiced other than as specifically described.

What is claimed is:

1. A process for evaluating the tenderness of meat comprising the steps of measuring the concentration of at least two of several trace elements in the meat and correlating the concentrations of said trace elements as independent variables of a functional relationship having tenderness as the dependent variable.

2. A process according to claim 1 in which the step of measuring the concentration of at least two of several trace elements comprises the step of measuring the concentration of iron and zinc in a sample of a carcass.

3. A process according to claim 2 in which the step of measuring the concentrations of at least two of several trace elements in the meat includes the step of measuring the concentrations of at least two of several trace elements in a sample of a muscle from a carcass of a beef animal carcass.

4. A process according to claim 2 in which the step of correlating the concentrations of said trace elements as independent variables of a functional relationship having tenderness as the dependent variable comprises the steps of:
obtaining a plurality of samples of muscle from a plurality of different carcasses;
said step of obtaining a plurality of samples including the step of obtaining a plurality of samples of the same muscle for the same species of animal;
obtaining the STR for a portion of each of said samples from a standard test panel;
measuring the concentrations of said trace elements from another portion of each of said samples; and
comparing the concentrations of the measured trace elements for each of said samples as independent variables with the STR for the same sample as a dependent variable in a regression to obtain a formula relating STR's as dependent variables with the concentrations of said measured trace elements.

5. A process according to claim 4 in which a carcass of the same species of animal is graded by:
taking a sample of the muscle of the carcass;
measuring the concentrations of the trace element in the sample;
substituting the concentrations of the trace elements into the formula; and
calculating an STR from the formula.

6. A process according to claim 4 in which said samples are samples taken from a beef animal carcass.

7. A process according to claim 2 in which the step of measuring the concentrations of at least two of several trace elements further includes the step of measuring the concentration of calcium in a portion of the same sample of said carcass.

8. A process according to claim 7 in which the step of measuring the concentration of at least two of several trace elements in the meat includes the step of measuring the concentration of at least two of several trace elements in a sample of a muscle from a carcass of a beef animal carcass.

9. A process according to claim 8 in which the step of correlating the concentrations of said trace elements as independent variables of a functional relationship having tenderness as the dependent variable includes the step of multiplying the ratio of the concentrations of iron to zinc by a first constant and subtracting the product from a second constant, wherein the first constant is substantially 4.5199 and the second constant is substantially 6.2386.

10. A process according to claim 7 in which the step of correlating the concentrations of said trace element as an independent variable of a functional relationship having tenderness as the dependent variable comprises the steps of:
obtaining a plurality of samples of muscle from a plurality of different carcasses;
said step of obtaining a plurality of samples including the step of obtaining a plurality of samples of the same muscle for the same species of animal;
obtaining the STR for a portion of each of said samples from a standard test panel;
measuring the concentration of said trace element from another portion of each of said samples;
comparing the concentrations of the measured trace elements for each of said samples as independent variables with the STR for the same sample in a multiple regression including all of said samples to obtain a formula correlating STR's as dependent variables with the concentration of said measured trace elements;
substituting the concentration of said at least two of several trace elements in the meat into said formula, whereby a calculated STR is obtained.

11. A process according to claim 7 in which the step of measuring the concentrations of at least two of several calcification-influencing trace elements includes the steps of:
mechanically homogenizing a portion of said muscle sample; exciting said homogenized sample by an X-ray source, whereby fluoresced photons from the iron and zinc atoms are quantified as needed to provide an arithmetic ratio of the abundances of each element in the sample muscle; and
obtaining an arithmetic ratio of the abundance of zinc and iron in the sampled muscle.

12. A process according to claim 10 in which the step of measuring the concentrations of at least two of several trace elements includes the steps of:
mechanically homogenizing a portion of said muscle sample;
exciting said homogenized sample by an X-ray source, whereby fluoresced photons from the iron and zinc atoms are quantified as needed to provide an arithmetic ratio of the abundances of each element in the sampled muscle;
obtaining an arithmetic ratio of the abundance of zinc and iron in the sampled muscle.

13. A process according to claim 1 in which the step of measuring includes the step of obtaining the ratio of iron to zinc in the muscle semimembranous of a beef carcass and the step of correlating includes the step of calculating a STR from the formula $$STR = -A \times \frac{iron\%}{zinc\%} + B,$$

where A is substantially 4.5199 and B is substantially 6.2386.

14. A process according to claim 1 in which the step of measuring includes the step of obtaining by measurement the ratios of iron to cobalt, silicon to cobalt and iron to zinc in the muscle semimembranous of a head of cattle and the step of correlating includes the step of calculating a STR from the formula $$STR = A \times \frac{iron\%}{cobalt\%} + B \times \frac{silicon\%}{cobalt\%} - C \times \frac{iron\%}{zinc\%}$$

where A is substantially 0.0543, B is substantially 0.0503, and C is substantially 6.6418 and A is 1.1557.

15. A process according to claim 1 in which the step of measuring includes the step of obtaining by measurement the concentrations of iron, silicon, zinc and calcium in the muscle semimembranous of a head of cattle and the step of correlating includes the step of calculating a STR from the formula:

$$STR = E \times 1 + A \times zinc - B\, calcium - C \times iron - D \times silicon$$

where A is substantially 0.0772, B is substantially 0.1362, C is substantially 0.1933, D is substantially 0.0116 and E is substantially 13.0741.

16. A process according to claim 1 in which the step of measuring includes the step of obtaining by measurement the ratios of iron to calcium, silicon to calcium and iron to zinc in the muscle semimembranous of a head of cattle and the step of correlating includes the step of calculating a STR from the formula:

$$STR = D \times 1 - A \times \frac{iron}{zinc} + B \times \frac{iron}{calcium} + C \times \frac{silicon}{calcium}$$

where D is substantially 4.1076, A is substantially 5.6932, B is substantially 1.1783 and C is substantially 2.6509.

17. A process according to claim 1 in which the step of measuring includes the step of obtaining by measurement the concentrations of calcium, cadmium, lead, cobalt, copper, zinc, iron and selenium in the muscle semimembranous of a head of cattle and the step of correlating includes the step of calculating a STR from the formula:

$$\begin{aligned}STR = &- A \times \%calcium - B \times \%cadmium \\ &- C \times \%lead + D \times \%cobalt \\ &- E \times \%copper + F \times \%zinc \\ &- G \times \%iron + \%selenium \\ &+ 1\end{aligned}$$

where A is substantially $0.1054 \times 10^4$, B is substantially $59.0651 \times 10^4$, C is substantially $0.7538 \times 10^4$, D is substantially $4.9301 \times 10^4$, E is substantially $3.2299 \times 10^4$, F is substantially $0.1065 \times 10^4$, G is substantially $0.0806 \times 10^4$, H is substantially $4.0808 \times 10^4$ and I is substantially 9.7360.

18. The process according to claim 1 in which the step of correlating the concentrations of said trace elements includes the steps of correlating the ratio of the concentrations of said two trace elements as independent variables of a functional relationship having tenderness as the dependent variable.

19. A process according to claim 1 in which the step of correlating the concentrations of said trace elements as independent variables of a functional relationship having tenderness as the dependent variable comprises steps of:
obtaining a plurality of samples of muscle from a plurality of different carcases;
said step of obtaining the plurality of samples including the step of obtaining a plurality of samples of the same muscle for the same species of animal;
measuring the tenderness of a portion of each of said samples using a standard measuring technique for tenderness;
measuring the concentrations of said trace elements from another portion of said samples; and
comparing concentrations of the measured trace elements for each of said samples as independent variables with the measured tenderness for the same sample as a dependent variable in a regression to obtain a formula relating the measured tenderness as dependent variables with the concentration of said measured trace elements.

20. A process according to claim 19 in which the step of obtaining a measurement of tenderness using a standard technique for measuring tenderness includes the step of obtaining the STR for a portion of each of said samples from a standard test panel.

21. A process according to claim 20 in which a carcass of the same species of animal is graded by:
taking a sample of the muscle of the carcass;
measuring the concentrations of the trace element in the sample;
substituting the concentrations of the trace element into the formula; and
calculating an STR from the formula.

22. A process according to claim 19 in which the step of obtaining a plurality of samples of the same muscle for the same species of animal includes the step of obtaining samples from a beef animal carcass.

* * * * *